United States Patent
Vollert

(10) Patent No.: US 10,213,450 B2
(45) Date of Patent: Feb. 26, 2019

(54) COMBINATION OF BIOLOGICALLY ACTIVE SUBSTANCES FOR TREATMENT OF HYPERGLYCAEMIC DISORDERS

(71) Applicant: BioActive Food GmbH, Bad Segeberg (DE)

(72) Inventor: Henning Vollert, Bad Segeberg (DE)

(73) Assignee: BioActive Food GmbH, Bad Segeberg (DE)

( * ) Notice: Subject to any disclaimer, the term of this patent is extended or adjusted under 35 U.S.C. 154(b) by 0 days.

(21) Appl. No.: 15/311,747

(22) PCT Filed: May 15, 2015

(86) PCT No.: PCT/EP2015/060743
§ 371 (c)(1),
(2) Date: Nov. 16, 2016

(87) PCT Pub. No.: WO2015/173383
PCT Pub. Date: Nov. 19, 2015

(65) Prior Publication Data
US 2017/0080005 A1  Mar. 23, 2017

(30) Foreign Application Priority Data
May 16, 2014 (EP) .................................. 14168754

(51) Int. Cl.
| | |
|---|---|
| *A01N 43/04* | (2006.01) |
| *A61K 31/70* | (2006.01) |
| *A61K 31/7034* | (2006.01) |
| *A61K 31/7048* | (2006.01) |
| *A23L 33/10* | (2016.01) |
| *A61K 31/352* | (2006.01) |

(52) U.S. Cl.
CPC .......... *A61K 31/7034* (2013.01); *A23L 33/10* (2016.08); *A61K 31/352* (2013.01); *A61K 31/7048* (2013.01); *A23V 2002/00* (2013.01)

(58) Field of Classification Search
None
See application file for complete search history.

(56) References Cited

FOREIGN PATENT DOCUMENTS

| EP | 2679229 | 1/2014 |
|----|---------|--------|
| WO | 2007124102 | 11/2007 |
| WO | 2012168108 | 12/2012 |

OTHER PUBLICATIONS

Panda et al. BioFactors (2007), vol. 31, pp. 201-210.*
International Search Report and Written Opinion in related PCT/EP2015/060743, dated Jul. 14, 2015, 10 pages (translation attached).
Lee, et al., "Major Phenolics in Apple and Their Contribution to the Total Antioxidant Capacity", J. Agric. Food Chem., 2003, vol. 51, issue 22, pp. 6516-6520 (abstract attached).
Ehrenkranz, et al., "Phlorizin: a review", Diabetes Metab. Res. Rev., Jan.-Feb. 2005, vol. 21, issue 1, pp. 31-38 (abstract attached).
Kamalakkanman, et al., "Antihyperglycaemic and Antioxidant Effect of Rutin, a Polyphenolic Flavonoid, in Streptozotocin-Induced Diabetic Wistar Rats", Basic & Clinical Pharmacology & Toxicology, 2006, vol. 98, pp. 97-103.
Kim, et al., "Quercetin attenuates fasting and postprandial hyperglycemia in animal models of diabetes mellitus", Nutr. Res. Pract., 2011, vol. 5, issue 2, pp. 107-111.
Zhang, et al., "Flavonol kaempferol improves chronic hyperglycemia-impaired pancreatic beta-cell viability and insulin secretory function", Eur. J. Pharmacol., Nov. 16, 2011, vol. 670, issue 1, pp. 325-332 (abstract attached).
Zang, et al., "Anti-Diabetic Effects of a Kaempferol Glycoside-Rich Fraction from Unripe Soybean (Edamame, *Glycine max* L. Merrill. 'Jindai') Leaves on KK-Ay Mice", Biosci. Biotechnol. Biochem., 2011, vol. 75, issue 9, pp. 1677-1684.

* cited by examiner

*Primary Examiner* — Patrick T Lewis
(74) *Attorney, Agent, or Firm* — Hovey Williams LLP

(57) ABSTRACT

The present invention relates to a synergistic composition which comprises (a) phlorizin, and (b) at least one further defined inhibitor of the enzyme lactase-phlorizin hydrolase. In particular, the present invention relates to such a composition for the treatment and/or prophylaxis of a hyperglycemic disease such as obesity, diabetes or a secondary disease associated with diabetes. The invention further relates to the use of such a composition for preparing a pharmaceutical composition, a dietary foodstuff and/or a food supplement. The invention further relates to pharmaceutical compositions, dietetic foods and food supplements which comprise a composition according to the present invention.

7 Claims, No Drawings

COMBINATION OF BIOLOGICALLY ACTIVE SUBSTANCES FOR TREATMENT OF HYPERGLYCAEMIC DISORDERS

RELATED APPLICATIONS

This application is the National Stage of International Patent Application No. PCT/EP2015/060743, filed May 15, 2015, which is hereby incorporated by reference in its entirety, and which claims priority to European Patent Application No. 14168754.1, filed May 16, 2014.

The present invention relates to a synergistic composition which comprises (a) phlorizin, and (b) at least one further defined inhibitor of the enzyme lactase-phlorizin hydrolase. In particular, the present invention relates to such a composition for the treatment and/or prophylaxis of a hyperglycemic disease such as obesity, diabetes or a secondary disease associated with diabetes. The invention further relates to the use of such a composition for preparing a pharmaceutical composition, a dietary foodstuff and/or a food supplement. The invention further relates to pharmaceutical compositions, dietetic foods and food supplements which comprise a composition according to the present invention.

FIELD OF THE INVENTION

The number of diabetes deaths has increased, according to the Federal Statistical Office since 1980 by 29 percent. Diabetes mellitus is thus responsible for about three percent of all deaths (1980: two percent) in Germany. In parallel, the number of obese people in Germany rises sharply. Every second German is already overweight, one in five are obese. In these people, the risk of developing diabetes is dramatically increased.

Current projections predict that up to 7% of Germans (Hauner H. Dtsch Med Wochenschr 2005; 130 Suppl 2: S.64-65), i.e. around 6 million people, are treated for diabetes. The number of new cases increases with increasing age. In the age group over 60 years the proportion of diabetes patients is already at 18-28%. In parallel, the age at which Type 2 diabetes occurs is steadily decreasing. Type 2 diabetes is with approximately 11% the fourth most common diagnosis of primary care internists and with around 8% the fifth most common diagnosis of all general practitioners (Wittchen HU, (HYDRA) study, Fortschr Med Orig 2003; 121). Current WHO estimates assume that the number of diabetes patients is expected to double by 2025 (World Health Organization, diabetes mellitus, Fact sheet No. 138, 2002).

With the food a variety of fats, carbohydrates and proteins is ingested, which provide the human body with the required energy. Too much intake and especially too rapid absorption of sugars constitutes a heavy burden for the metabolism and is considered a major risk factor for diabetes, overweight and obesity. There is therefore a continuing need for new agents for the treatment of hyperglycemic disorders such as diabetes and obesity.

Numerous classes of compounds have been proposed for the treatment of diabetes mellitus, particularly diabetes mellitus type II. For example, substances have been suggested in various international applications which inhibit the sodium-dependent glucose transporter 2 (SGLT-2) (see e.g. WO 98/31697, WO 02/083066, WO 03/099836 and WO 01/31697). This transport protein resorbs glucose and sodium from the primary urine in the proximal tubule of the kidney. Specific SGLT-2 inhibitors are able to inhibit the intake of glucose into the renal tubules, resulting in restoration of normal plasma glucose levels. In animal studies, a long-term treatment with SGLT-2 inhibitors of more than 6 months has resulted in increased insulin sensitivity, an improved insulin response and a delayed formation of diabetes-related complications. The inhibition of the transporter SGLT-2 is based on an increased concentration-dependent excretion of glucose, resulting in lowering blood sugar in the body. However, no hypoglycemia is caused. The mechanism of blood glucose lowering is independent of any existing insulin resistance or a lack of insulin production by the pancreatic beta cells. Besides SGLT-2, there is another sodium-dependent glucose transporter, SGLT-1, which is also associated with the treatment of diabetes. SGLT-1 is found in the small intestine and in the S3 segment of the proximal tubule. It is responsible for the active uptake of glucose. Compared to SGLT-2, SGLT-1 exhibit altered substrate specificity for some sugars. Some preparations that lead to inhibition of SGLT-1 and/or SGLT2 are currently in clinical trials.

European Patent Application 12174534.3 describes the use of a composition comprising an extract of a plant of the genus *Brassica* in combination with phlorizin or a phlorizin-containing extract. The composition is proposed for the treatment of hyperglycemic disorders.

DESCRIPTION OF THE INVENTION

In the course of the present invention, it has now been found that an advantageous synergistic effect can be obtained on the blood sugar level if, in addition to inhibiting the sodium-dependent glucose transporter SGLT1 by phlorizin, the enzyme lactase phlorizin hydrolase (LPH) is inhibited by an inhibitor as described herein. A combined administration of phlorizin and an inhibitor of LPH as defined herein leads to a significantly lower increase in blood glucose concentration after the intake of foods with a high proportion of carbohydrates, such as starch, and therefore is highly suitable for the treatment and/or prophylaxis of hyperglycemic metabolic diseases such as diabetes and/or obesity.

The enzyme LPH is well described in the prior art and is synthesized in the intestine of mammals. The enzyme is present as an integral membrane protein in the brush border of the main cells of the epithelium of the villi of the small intestine of all mammals. It catalyzes in the intestinal lumen the cleavage of beta-glycosidic bonds in carbohydrates such as lactose. In addition to hydrolyzing phlorizin, the LPH is also able to cleave the disaccharide lactose into the monosaccharides glucose and galactose. These two different activities of the enzyme occur at different reactive centers of the LPH. According to the invention, an inhibitor of the LPH is in particular able to inhibit the phlorizin-cleaving enzymatic activity of the LPH, preferably that of the human LPH. It is preferred that the inhibitor reduces this activity of the LPH by at least 5%, 10%, 15%, more preferably by at least 20%, 25%, 30% or more preferably by at least 40%, 50%, 60%, 70% or 80%. The skilled person is familiar with methods by which the activity of LPH and accordingly also its inhibition can be determined. Such methods are also described in the examples of the present application.

The inhibitor(s) of the LPH employed in the present invention are flavonol glycosides, which have a quercetin or kaempferol backbone and are connected via a glycosidic bond with at least one sugar group. Consequently, the inhibitors according to the present invention are quercetin or kaempferol glycosides.

In a first aspect the invention relates to compositions that contain at least the following components: (a) phlorizin and (b) at least one inhibitor of the lactase phlorizin hydrolase, wherein the inhibitor is a glycoside of a flavonol having the structure according to formula I:

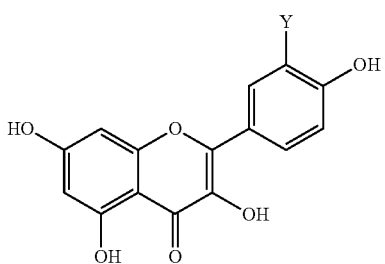

I wherein Y is selected from the group consisting of H and OH; and wherein the inhibitor comprises at least one sugar group that is glycosidically bound to the flavonol.

Flavonols are a subgroup within the chemical group of flavonoids. Flavonoids belong to the group of secondary plant products, and they represent a large class of polyphenolic compounds which widely occur in food of plant origin.

In the present invention, it has now been found that glycosides of a flavonol of formula I are effective inhibitors of the LPH. The above mentioned formula I shows the basic structure of the flavonols kaempferol and quercetin. If Y is H, formula I corresponds to kaempferol. If Y is an OH group, formula I corresponds to quercetin. It is thus preferred according to the invention that the inhibitor of the LPH is a glycoside of kaempferol or a glycoside of quercetin.

The substance of formula I which is effective as an inhibitor of the LPH has at least one sugar group which is glycosidically bound to the flavonol. The LPH inhibitor therefore is a glycoside having the formula I. Glycosides according to the present invention are compounds which comprise a glycosidically bound sugar group and have the general structure R—O—Z, wherein Z is the sugar residue and R is the aglycone. Any type of sugar that can bind via glycosidic binding to formula I may be employed in the LPH inhibitors of the invention. The glycosidically bound group may, for example, be a mono- or polysaccharide, such as a disaccharide or trisaccharide.

It is preferred according to the invention that the group which is glycosidically bound is a monosaccharide. The monosaccharide, which is glycosidically linked to the flavonol according to formula I, can be for example a monosaccharide selected from the group consisting of glucose, fructose, rhamnose, glucopyranose, mannose, and galactose. The monosaccharide is preferably glucose. Thus, in a preferred embodiment the present invention relates to a composition comprising (a) phlorizin, and (b) at least one inhibitor of the LPH, wherein the inhibitor is a glycoside of a flavonol of formula I, and wherein Y is selected from the group consisting of H and OH; and wherein the inhibitor comprises at least one glucose group that is glycosidically bound to the flavonol. In such embodiment, the inhibitor of the LPH is thus a glucoside. A glucoside is a compound comprising a glycosidically-bound glucose residue and having the general structure R—O-Glc, wherein said Glc is a glucose residue and R is the aglycone.

In a further preferred embodiment, the sugar group which is glycosidically bound to the compound of formula I is a polysaccharide. Suitable polysaccharides include, for example, di-, tri-, tetra- and pentasaccharides. Suitable disaccharides are, for example, cellobiose, gentiobiose, isomaltose, isomaltulose, lactose, lactulose, laminaribiose, maltose, maltulose, melibiose, neohesperidose, neotrehalose, nigerose, rutinose, sambubiose, sophorose, saccharose, and trehalose. Suitable trisaccharides are, for example, fucosidolactose, gentianose, isokestose (1-kestose), kestose (6-kestose), maltotriose, manninotriose, melezitose, neokestose, panose, raffinose, and umbelliferose. In a preferred embodiment, the polysaccharide that is bound to the flavonol is rutinose.

The glycosidically bound sugar group is preferably bound beta-glycosidically to the flavonol. It is especially preferred that the glycosidic binding of the sugar group is effected via one of the OH groups in position 3', 4', 3, 5 or 7 shown in the formula I. The numbering of the positions in the flavonol follows the generally known chemical nomenclature, as indicated in the following formula II:

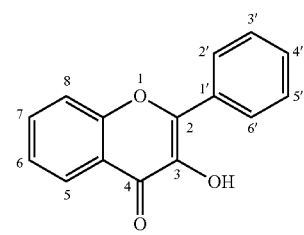

II

In a preferred embodiment, the glycosidically bound group of the inhibitor is in position 7 of the flavonol. In a further preferred embodiment, the glycosidically bound group of the inhibitor is in position 3 of the flavonol. In yet another preferred embodiment, the inhibitor comprises only a single glycosidically bound sugar group, which is in position 3 of the flavonol. In yet another preferred embodiment, the inhibitor comprises only a single glycosidically bound sugar group, which is located in position 7 of the flavonol. This means that the inhibitor in these embodiments, apart from the glycosidically bound group in position 3 or 7 of the flavonol, does not contain any additional glycosidically bound group.

According to the invention, the LPH-inhibitor may also comprise a plurality of sugar groups, each of which is bound via glycosidic binding to the flavonol according to formula I. For example, the LPH inhibitor may comprise 2, 3, 4, 5 or more sugar groups linked in this way. These glycosidically linked sugars will also preferably be bound via one of the OH groups in position 3', 4', 3, 5 or 7 depicted in formula I.

The inhibitor of the LPH may in particular be one of the following molecules: quercetin-7-O-glucoside, kaempferol-7-O-glucoside, quercetin-3-O-rhamnoside, quercetin-3-O-glucopyranoside, kaempferol-3-O-glucoside, kaempferol-3-O-rutinoside, quercetin-3-galactoside, quercetin-4'-glucoside, quercetin-3-O-rutinoside (quercetin-3-O-glucorhamnoside), kaempferol-3,7-di-O-α-L-rhamnoside, kaempferol-3-(2G-xylosylrutinoside), 3-glucosyl-quercetin, 3-glucosyl-kaempferol, dihydro-kaempferol-3-rhamnoside, quercetin-3,4-O-glucoside, 4'-methyl-kaempferol, kaempferol-3-O-feruloyl-diglucoside-7-O-glucoside, kaempferol-3-O-hydroxyferuloyl-diglucoside, kaempferol-3-O-disinapoyl-triglucosid-7-O-diglucoside, kaempferol-3-O-sinapoyl-triglucoside, kaempferol-3-O-sinapoyldiglucoside, kaempferol-3-O-disinapoyl-triglucosid-7-O-glucoside, kaempferol-3-O-diglucoside-7-O-diglucoside, kaempferol-3-O-triglucosid-7-O-glucoside, kaempferol-3-O-glucoside-7-O-glucoside, kaempferol-3-O-triglucoside, kaempferol-3-O-diglucoside, kaempferol-3-O-glucoside, and the like.

In a particularly preferred embodiment, the LPH-inhibitor is quercetin-7-O-glucoside. In another embodiment, the LPH inhibitor is kaempferol-7-O-glucoside.

In addition, the LPH inhibitors of the present invention may also be SGLT1 inhibitors so that they exert a dual effect. Examples of such dual inhibitors are for example quercetin-7-O-glucoside and kaempferol-7-O-glucoside.

The sugar group glycosidically bound to the flavonol may have further modifications. Thus, the sugar group is acylated in one embodiment, i.e., the sugar group includes one or more acyl groups. Preferred acylated inhibitors of lactase phlorizin hydrolase are, for example, selected from the group consisting of kaempferol-3-O-hydroxyferuloyl-tetraglucoside, kaempferol-3-O-hydroxyferuloyl-diglucoside-7-O-hydroxyferuloyl-diglucoside, kaempferol-3-O-hydroxyferuloyl-diglucoside-7-O-glucoside, kaempferol-3-O-sinapoyl-diglucoside-7-O-diglucoside and kaempferol-3-O-sinapoyl-diglucoside-7-O-glucoside. In a particularly preferred embodiment, the inhibitor is kaempferol-3-O-sinapoyl-diglucoside-7-O-diglucoside.

It is preferred according to the invention that the sugar group which is glycosidically bound to the flavonol is an acylated polysaccharide.

In addition, a sugar group bound to the flavonol may be a cinnamic acid derivative, i.e., the sugar group includes one or more groups which have been derived from cinnamic acid, for example a hydroxy cinnamic acid, such as a sinapic acid group (3,5-dimethoxy-4-hydroxy-cinnamic acid), α-cyano-4-hydroxy-cinnamic acid (HCCA) group, a ferulic acid group (4-hydroxy-3-methoxy cinnamic acid) and a caffeic acid group. In this embodiment, the sugar group is, for example, present as a sinapoyl glycoside or feruloyl glycoside.

The compositions of the invention comprise, in addition to one or more inhibitors of the LPH the flavonoid phlorizin. Phlorizin inhibits the transporter SGLT 1 in vitro (Kottra et al. (2007), J Pharmacol Exp Ther, 322 (2): 829-35). It is also long known that phlorizin acts on the glucose excretion of the kidney when it is administered intravenously. However, the effect is weak when phlorizin is administered orally. This is probably in part due to an enzymatic degradation of the phlorizin in the intestine, which is catalyzed, for example, by the enzyme LPH (Birkenmeier & Alpers (1974), Biochim Biophys Acta, 350 (1):100-12). After intake of the composition of the invention, the enzymatic degradation of phlorizin in the intestine is inhibited by the above defined inhibitor(s) of LPH, whereby the phlorizin exerts its inhibitory properties on glucose uptake (SGLT 1).

The compositions of the invention contain an amount of phlorizin which is effective to inhibit after oral administration the glucose transporter SGLT-1 and/or to slow down sugar absorption from the intestine. In a preferred embodiment, the activity of the SGLT-1 transporter present in the intestine is reduced by the compositions by at least about 1%, 2%, 3%, 4%, 5%, 10%, 20%, 30%, 40%, 50%, 60%, 70%, 80%, 90% or more reduced compared to the untreated state. In a further preferred embodiment, the composition according to the invention leads after administration to sugar absorption from the intestine which is reduced by at least about 1%, 2%, 3%, 4%, 5%, 10%, 20%, 30%, 40%, 50%, 60%, 70%, 80%, 90% or more compared to the untreated state.

The skilled person is readily able to determine the amount of phlorizin and LPH inhibitor required for the (therapeutic) effect to be achieved by simple test series. Here, the skilled person will take into account various factors, for example, the type and amount of the inhibitor(s) of LPH present in the composition, the type and amount of the additional components present in the compositions, the age and weight of the person to whom the composition is administered, etc.

The amount of phlorizin in the compositions according to the invention is preferably greater than 1 ppm (parts per million) or 0.0001% (w/w). It is preferred that the amount of phlorizin in the composition is greater than 10 ppm, greater than 100 ppm, greater than 1000 ppm, greater than $10^4$ ppm, greater than $5 \cdot 10^4$ ppm or greater than $10^5$ ppm. In other words, the composition of the invention contains more than 0.0001% (w/w), more than 0.001%, preferably more than 0.01%, more than 0.1%, more than 1%, more than 2%, more than 3%, more than 4%, more than 5%, more than 6%, more than 7%, more than 8%, more than 9%, more than 10%, more than 11%, more than 12%, more than 13%, more than 14%, or more than 15% phlorizin. It is also preferred that the composition according to the invention comprises more than 20% (w/w), more than 25%, more than 30%, more than 35%, more than 40%, more than 45%, more than 50%, more than 55%, or more than 60% phlorizin. In a particularly preferred embodiment, the compositions of the invention comprise between 1-95% (w/w), for example 5-80%, 10-70%, 15-60%, 20-50%, or 30-40% phlorizin, or for example 5-95%, 10-95%, 15-95%, 20-95%, or 30-95% phlorizin.

The composition of the invention is preferably formulated such that the respective delivery unit (e.g. a capsule, a tablet or a defined amount of a liquid) contains a quantity of 0.01 to 10 g phlorizin, e.g. more than 0.05 g, more than 0.1 g, more than 0.2 g, more than 0.3 g, more than 0.4 g, more than 0.5 g, more than 0.75 g, more than 1 g, more than 2 g, more than 3 g, more than 4 g or more than 5 g.

The compositions according to the invention further contain an amount of LPH-inhibitor that is effective to inhibit lactase phlorizin hydrolase after oral administration. In a preferred embodiment, the activity of the intestinal LPH is reduced by the compositions by at least about 1%, 2%, 3%, 4%, 5%, 10%, 20%, 30%, 40%, 50%, 60%, 70%, 80%, 90% or more compared to the untreated state.

The amount of the LPH-inhibitor in the compositions according to the invention is also preferably greater than 1 ppm (parts per million) or 0.0001% (w/w). It is preferred that the amount of an LPH inhibitor in the composition is greater than 10 ppm, greater than 100 ppm, greater than 1000 ppm, greater than $10^4$ ppm, greater than $5 \cdot 10^4$ ppm or greater than $10^5$ ppm. In other words, the composition of the invention contains more than 0.0001% (w/w), more than 0.001%, preferably more than 0.01%, more than 0.1%, more than 1%, more than 2%, more than 3%, more than 4%, more than 5%, more than 6%, more than 7%, more than 8%, more than 9%, more than 10%, more than 11%, more than 12%, more than 13%, more than 14%, or more than 15% LPH inhibitor. It is also preferred that the composition according to the invention comprises more than 20% (w/w), more than 25%, more than 30%, more than 35%, more than 40%, more than 45%, more than 50%, more than 55%, or more than 60% of the LPH inhibitor defined herein. In a particularly preferred embodiment, the compositions of the invention contain between 1-95% (w/w), such as 5-80%, 10-70%, 15-60%, 20-50% or 30-40% LPH inhibitor, or such as 5-95%, 10-95%, 15-95%, 20-95%, or 30-95% LPH inhibitor.

In one embodiment, the LPH inhibitor that is present in the above amounts in the composition of the invention is kaempferol-7-O-glucoside. In another embodiment, the LPH inhibitor that is present in the above amounts in the composition of the invention is quercetin-7-O-glucoside.

The inventive composition is preferably formulated such that the respective delivery unit (e.g. a capsule, a powder, a tablet or a defined amount of a liquid) contains a quantity of 0.01 to 10 g LPH inhibitor, e.g. more than 0.05 g, more than 0.1 g, more than 0.2 g, more than 0.3 g, more than 0.4 g, more than 0.5 g, more than 0.75 g, more than 1 g, more than 2 g, more than 3 g, more than 4 g or more than 5 g.

It is particularly preferred that the composition of the invention is formulated for oral administration and contains from 0.01 to 10 g LPH inhibitor, preferably from 1-3 g LPH inhibitor, and from 0.01 to 10 g phlorizin, preferably from 1-3 g phlorizin.

According to another embodiment of the invention, the amount of phlorizin in the composition is at least 0.1 g, and the amount of the LPH inhibitor according to the above formula I in the composition is also at least 0.1 g. In another embodiment of the invention, the amount of phlorizin in the composition is at least 1 g, and the amount of flavonol glycoside according to the above formula I in the composition is also at least 1 g. In still another embodiment, the amount of phlorizin in the composition is between 0.1 and 1 g, and the amount of the LPH inhibitor according to the above formula I in the composition is also between 0.1 and 1 g.

Phlorizin and LPH-inhibitor(s) can be used in any mixing ratio. The amounts of phlorizin and LPH inhibitor in the compositions of the invention are however preferably combined by the skilled person such that an optimal effect is achieved, i.e. both LPH and SGLT1 be inhibited efficiently. In one embodiment, the composition of the invention comprises phlorizin and LPH inhibitor(s) in a ratio of about 20:1, 10:1, 5:1, 4:1, 3:1, 2:1, 1:1, 1:2, 1:3, 1:4, 1:5, 1:10 or 1:20. A mixing ratio between phlorizin and the LPH inhibitor(s) of 1:1 is particularly preferred.

In a particularly preferred embodiment of the invention, the composition of the invention is not a plant or part of a plant, e.g. a fruit. In one particularly preferred embodiment, the LPH inhibitor of the composition of the invention is not added in the form of a plant extract. If the LPH inhibitor originally stems from a plant extract, the inhibitor was purified from the extract prior to its use in the compositions of the present invention. Alternatively, the LPH inhibitor may also be a compound which has been obtained by chemical synthesis. Methods for the chemical synthesis of the inhibitory flavonol compounds indicated above are known in the art and have been described in the literature, see e.g. Hirpara et al. (2009, Anticancer Agents Med Chem, 9 (2): 138-61).

Furthermore, it is preferred that the above defined LPH inhibitors and phlorizin in total account for more than 70% (w/w), preferably more than 80%, 85%, 90%, 95% or 99%, of the flavonoid glycosides that are present in the composition of the invention. This means that the composition of the invention contains less than 30% (w/w), preferably less than 20%, 15%, 10%, 5% or 1%, flavonoid glycosides which are not the above defined LPH inhibitors or phlorizin. In a particularly preferred embodiment, the composition of the invention contains less than 1% (w/w) or no flavonoid glycosides, which are not the above-defined LPH inhibitors or phlorizin.

According to the invention, it is particularly preferred that both the phlorizin used in the compositions according to the invention as well as the LPH inhibitor are prepared synthetically. In a further particularly preferred embodiment, neither the phlorizin nor the LPH inhibitor is in the form of a plant extract.

In another embodiment, the phlorizin is added to the LPH inhibitor(s) in the form of a phlorizin-containing plant extract. The phlorizin-containing plant extract may be obtained, e.g. from at least one plant of the family Rosaceae. Preferably, the plant of the family Rosaceae belongs to a genus which is selected from the group consisting of *Malus*, *Pyrus* or *Prunus*. The phlorizin-containing plant extract may further also be from a plant of the family Verbenaceae. Preferably, the plant of the family Verbenaceae is from the genus *Lippia*. It is known that in particular plants of these families contain phlorizin. The extract of the plant from the family Rosaceae or Verbenaceae may be obtained, for example, from the bark, fruits, or leaves of the plant.

Plants of the genera *Malus, Pyrus* and *Prunus* contain relatively high amounts of phlorizin in the bark, fruits and leaves. In particular, the fruits of the genus *Malus* (i.e. apples) have particularly high levels of phlorizin. It is therefore particularly preferred that the phlorizin in the composition of the invention is present in the form of an extract from a plant of the genus *Malus*, preferably in the form of an extract from apples or the bark. The genus *Malus* is a plant genus in the rose family (Rosaceae). It is particularly preferred that the extracts are prepared from a plant of the genus *Malus* starting from plants of the species *Malus domestica*. The culture apple (*Malus domestica* Borkh.; *Pyrus malus*, L.) is an economically very important fruit species with numerous varieties. In principle, all varieties of the culture apple can be used for the preparation of the phlorizin-containing extracts. It is particularly preferred that the extracts are produced from one of the varieties Red Delicious, Golden Delicious, Braeburn, Cox Orange, Finkenwerder Prinz, Fürst Blücher, Märkischer Cox or Red Chief. In addition to plants of the species *Malus domestica*, however, other species of the genus *Malus* may be used.

It is preferred that the at least one extract of the plant from the family of Rosaceae and/or the at least one extract from the family of Verbenaceae contain at least 1%, preferably at least 2%, 3%, 4%, 5%, 6%, 7%, 8%, 9%, 10%, 15%, 20% or more phlorizin (w/w).

In a further preferred embodiment, the compositions comprise one or more LPH inhibitors according to the invention and at least one extract from at least one plant of the family *Rosaceae* and/or from at least one plant of the family *Verbenaceae*. In one embodiment, the compositions contain one or more, e.g., two, three, four or more, of the LPH inhibitors of the invention and/or more than one, e.g. two, three, four or more extracts of a plant of the genus *Malus*. Especially preferred are compositions that contain quercetin-7-O-glucoside and/or kaempferol-7-O-glucoside and at least one extract of a plant of the genus *Malus*. The term "extract of a plant" as used herein refers to an extract that is obtained from one or more plants of the same kind or species, respectively, and is not limited to a single plant.

As used here, the term "extract" refers to a mixture of substances, which is obtained by rupture of cells of a plant and recovery of the cell juice. The proposed extracts of the invention can be prepared by a variety of methods known in the art.

In one embodiment of the invention, a plant material is first provided. As starting material for the process of the invention, plants in all stages of development are suitable, from the seed to the mature plant. In addition, all parts of plants are suitable, such as the fruits, stems, leaves, bark or roots of the plant. The starting material can be a mixture of different plant parts, or it may only include certain plant parts. The plant material is usually crushed first. The comminution can be achieved simply by chopping the respective parts of plants with conventional cutters. Basically, all plant parts can be used as a starting material for preparing the extract. For the preparation of extracts of plants of the genus *Malus*, the fruit and bark have been found to be particularly suitable. In a further preferred embodiment, the extracts from a plant of the genus *Malus* are prepared from the fruit, i.e. from the apples, or from the bark of the respective *Malus* plant. Before crushing, the plant material can be blanched at temperatures between 45° C. and 100° C., to eliminate bacterial contamination and improve the digestion quality. Furthermore, blanching reduces the activity of enzymes such as hydrolases, lipases and oxidases, thereby increasing the stability and quality of the plant material.

In a next step, the plant material is decomposed, i.e. the cellular structures of the material are destroyed so that the content of the cells is released. The digestion can be achieved by conventional methods for the digestion of plant cells, for example, by repeated freezing and thawing, or by suitable devices such as homogenizers, high-pressure homogenizers or ultrasonic homogenizers. Also colloid mills or French presses can be used for digestion.

In addition, the decomposition of the cells may also be achieved enzymatically. To this end, the plant material is treated with appropriate enzymes that lead to the destruction of the structural components of the cells. It has been shown that at this stage of the process incubation of the plant material with pectinase, collagenase, cellulase and/or hemicellulases is particularly suited to effectively decompose the cell. The incubation period can be between 30 minutes and 24 hours, preferably between 1 hour and 6 hours, more preferably between 90 minutes and 4 hours, e.g. 2 hours. The temperature may be in the range of 20° and 60° C., preferably between 25° C. and 45° C., e.g. at about 37° C., and it should preferably be in the range of the temperature optimum of the enzyme used in each case. A suitable pH value of the reaction mixture may be adjusted by using a suitable buffer such as phosphate, carbonate, sodium hydrogen carbonate buffer and/or suitable acids, such as citric acid, lactic acid or ascorbic acid. A pH of between 4 and 6, e.g. pH 5, is particularly suitable for the digestion.

After disruption of the cells, the cell juice so obtained can be directly used for inhibiting the sodium-dependent glucose transporter 1 (SGLT-1). However, it is preferred to subject the cell juice obtained after digestion of the cells to additional purification steps.

For example, the material obtained from the cell decomposition can be subjected to drying or lyophilization and subsequent extraction. Here, for example, spray drying may initially be used. The dried or freeze-dried plant material can then be extracted with an aqueous or organic solvent. The extraction can be carried out using a conventional extraction agent, e.g. with ethanol, ethyl acetate or with other organic solvents. Also, the extraction with gases such as nitrogen is possible. When using a liquid solvent, the incubation time is from 0.5 to 24 hours, preferably from 2 to 8 hours. If nitrogen is used, the extraction is carried out at temperatures between 4° C. and 37° C. over a period of 0.25 to 3 hours, preferably over a period of 20 and 60 minutes.

The compositions proposed according to the invention may be produced by a variety of methods known in the art. The LPH inhibitors of the invention and phlorizin can be prepared by methods known in the art or purchased directly from various manufacturers and mixed in the desired amounts with one another (e.g. from Carl Roth GmbH & Co. KG, Karlsruhe, Germany).

In a preferred embodiment, the phlorizin in the phlorizin-containing extract is concentrated. Methods for increasing the concentration of these substances are known to the skilled person and are described, for example, in Will et al. (2006, LWT—Food Science and Technology, 40(8): 1344-1351). A concentration of phlorizin can be achieved, for example, by using column chromatography. For example, various adsorber columns may be used for this purpose. The chromatography columns are loaded with the initial extract, and undesirable constituents are removed by flushing with suitable solutions, and then eluted in concentrated form from the column. For example, after loading of the adsorber columns with unconcentrated extract, hydrophilic substances (salts, amino acids, peptides, sugars, etc.) are depleted by rinsing with demineralized water. In the extract that was eluted with 95% ethanol, phlorizin is then enriched. The phlorizin extracts can be produced in both dry and liquid form.

The compositions of the invention are proposed according to the invention for the treatment and/or prophylaxis of a hyperglycemic disease. The compositions are distinguished by a synergistic action of their components, i.e. the interaction of the individual components is beyond a purely additive effect.

Diseases that can be treated using the compositions proposed according to the invention include all diseases caused by hyperglycemia, i.e. which are characterized by an elevated blood sugar level which exceeds the normal physiological value of 140 mg/dl (7.8 mmol/l). Such diseases include, in particular obesity, diabetes or a secondary disease caused by diabetes (such as retinopathy, neuropathy, nephropathy and abnormal wound healing). The diabetes to be treated by the compositions of the invention may be diabetes type I or type II. Preferably it is type II diabetes. Moreover, the compositions of the invention are generally proposed for the treatment and/or prophylaxis of diseases and conditions, where it is advantageous to slow down and/or reduce the sugar uptake from the intestine.

The compositions proposed according to the invention for the treatment or prophylaxis can also be used advantageously with other active ingredients, e.g. together with other anti-diabetic agents which have been described in the prior art, such as biguanide, sulfonylureas, glycosidase inhibitors, preferably inhibitors of carbohydrate-cleaving enzymes of the digestive tract (e.g. O-4,6-Didesoxy-4-[[1S-(1S,4R,5S,6S)-4,5,6-trihydroxy-3-(hydroxymethyl)-2-cyclohexen-1-yl]amino]alpha-D-glucopyranosyl-(1→4)-O-alpha-D-glucopyranosyl-(1→4)-D-glucopyranose (see DE 23 47 782), thiazolidinediones, dipeptidyl peptidase IV (DP4) inhibitors, meglitinides, glucagon-like peptide-1 (GLP-1), PTP1B inhibitors, glycogen phosphorylase inhibitors, glucose-6-phosphatase inhibitors, and SGLT1 and SGLT2 inhibitors which have been described in the following protective rights: WO 02/080936, WO 02/080935, JP 2000080041, EP 0 850 948 (propiophenon glucosides); WO 02/044192, WO 02/028872, WO 03/011880 and WO 01/068660 (2-glucopyranosyl oxybenzyl benzenes); WO 02/068440, WO 02/068439, WO 02/36602, WO 01/016147, WO 02/053573, WO 03/020737, WO 03/090783, WO 04/014932, WO 04/019958 and WO 04/018491 (glucopyranosyl oxypyrazoles); WO 01/074835 and WO 01/074834 (O-glycoside benzamides); WO 04/007517 (glucopyranosyl oxythiophenes); WO 03/099836, WO 01/027128 and US 2002/0137903 (C-aryl glycosides); DE 102 58 008 (fluorine glycoside derivatives); DE 10 2004 028 241.2 (fluorine glycoside derivatives of pyrazoles).

The compositions of the invention which contain at least phlorizin and one or more LPH inhibitor(s) will be formulated for combined or sequential administration. Therefore, the present invention also provides the use of phlorizin and one or more LPH inhibitor(s) according to the invention for the treatment and/or prophylaxis of a hyperglycemic disease, wherein the components are formulated for separate administration.

In one aspect, the present invention relates to the use of a composition as described above for the preparation of a pharmaceutical composition, a dietetic food, or a food supplement.

In a still further aspect, the present invention thus relates to a pharmaceutical composition, a dietetic food or a food supplement, which comprises a composition as described above comprising at least one LPH inhibitor according to the invention and phlorizin. The pharmaceutical composition, dietetic food or food supplement are suitable for use in a method of treatment and/or prophylaxis of a hyperglycemic disease, preferably selected from the group consisting of obesity, diabetes, or a secondary disease caused by diabetes, and in particular for the treatment and/or prophylaxis of type II diabetes.

A pharmaceutical composition comprising the composition of the invention may be formulated for oral, parenteral or topical administration. Such a pharmaceutical composition can be prepared by methods well known in the prior art. Such methods and suitable excipients and carriers are, for example, described in "Remington: The Science and Practice of Pharmacy", Lippincott Williams & Wilkins; 21st Edition (2005). The pharmaceutical compositions may have, for example, the form of granules, powders, tablets, capsules, syrup, suppositories, injections, emulsions, suspensions or solutions. The compositions can be formulated for various routes of administration, for example, for the oral, parenteral, topical, buccal, sublingual, transmucosal, rectal, subcutaneous, intrathecal, intravenous, intramuscular, intraperitoneal, nasal, intraocular or intraventricular administration. The formulation as an oral, parenteral or topical composition is particularly preferred. In a particularly preferred embodiment, the composition is formulated for oral administration. The pharmaceutical compositions may also be formulated as a sustained-release agent.

For oral, buccal and sublingual administration, solid formulations such as powders, suspensions, granules, tablets, pills, capsules and gel caps are normally used. These may, for example, be prepared by mixing the active ingredients (phlorizin and the one or more inhibitor(s) of the lactase phlorizin hydrolase according to the invention) with at least one additive or with at least one excipient. Such excipients and carriers are, for example, described in "Remington: The Science and Practice of Pharmacy", Lippincott Williams & Wilkins; 21st Edition (2005). For example, microcrystalline cellulose, methyl cellulose, hydroxypropyl methyl cellulose, casein, albumin, mannitol, dextran, sucrose, lactose, sorbitol, starch, agar, alginates, pectins, collagen, glycerides or gelatin may be used as additives or excipients. Further, compositions for oral administration comprise antioxidants (e.g. ascorbic acid, tocopherol or cysteine), lubricants (e.g. magnesium stearate), preservatives (e.g. paraben or sorbic acid), taste enhancers, disintegrants, binders, thickeners, dyes and similar substances.

Liquid formulations of the compositions of the invention that are suitable for oral administration may be presented, for example, as an emulsion, syrup, suspension or solutions. These formulations can be prepared using as a sterile liquid carrier (e.g. oil, water, alcohol, or combinations thereof) in the form of liquid suspensions or solutions. For oral or parenteral administration, pharmaceutically suitable surfactants, suspending agent, oils or emulsifiers may be added. Suitable oils for use in liquid dosage forms include, for example, olive oil, sesame oil, peanut oil, rapeseed oil and corn oil. Suitable alcohols include ethanol, isopropyl alcohol, hexadecyl alcohol, glycerol and propylene glycol. Suspensions may also comprise fatty acid esters, such as ethyl oleate, isopropyl myristate, fatty acid glycerides and acetylated fatty acid glycerides. Further, suspensions are often treated with substances such as mineral oil or petrolatum.

The present invention further relates to a dietetic food or a dietary supplement comprising a composition as defined above, i.e. a composition which contains phlorizin and one or more LPH inhibitor(s) according to the invention. The dietetic food or dietary supplement is especially suitable for the treatment and/or prophylaxis of the above-defined obesity, diabetes (especially type II diabetes) or a secondary disease caused by diabetes. The phlorizin may originate from at least one phlorizin-containing plant extract. The extract is preferably derived from a plant of the genus *Malus*, especially from a plant of the species *Malus domesticus*. It is particularly preferred that at least one extract has been obtained from a plant of the genus *Malus* from the apples or the bark of a *Malus* plant.

EXAMPLES

The following examples describe the effect of the compositions of the invention:

Example 1: In Vitro Inhibition of LPH by Quercetin and Kaempferol Derivates

Various quercetin and kaempferol derivates were tested in vitro as inhibitors of lactase phlorizin hydrolase (LPH). The testing was carried out according to Amiri et al. (2012, J Inherit Metab Dis, 35(6): 949-54). Here, tissue of the human small intestine (0.6 mg/ml) expressing the LPH was used. Phlorizin dihydrate served as the substrate. The released glucose was measured using a standard assay (Chu & Cheung, 1978, Clin Biochem, 11(4): 187-9).

Results:

The tested quercetin and kaempferol derivates showed a high inhibitory activity on the LPH and were able to inhibit LPH in a concentration-dependent manner (Table 1). Quercetin-7-glucoside and kaempferol-7-O-glucoside showed a particularly intensive inhibition of the LPH by about 70% at a concentration of 50 mg/ml.

TABLE 1

Inhibition of various glycosidases by quercetin and kaempferol derivates:

| No. | name inhibitor | Synonyms | Inhibition of LPH (10 µg/ml inhibitor) | Inhibition of LPH (50 µg/ml inhibitor) |
|---|---|---|---|---|
| 1 | quercitrin | quercetin-3-O-rhamnoside | Nd | 12.8% (100 µg/ml) |
| 2 | quercetin-3-glucopyranoside | quercetin-3-O-glucopyranoside | Nd | 13.7% (100 µg/ml) |
| 3 | quercetin-7-glucoside | 3,3',4',5,7-pentahydroxy flavone-7-glucoside | 44.0% | 69.4% |
| 4 | kaempferol-3-O-glucoside | astragalin | 3.3% | 45% |
| 5 | kaempferol-7-O-glucoside | populin | 53.0% | 70.5% |
| 6 | kaempferol-3-O-rutinoside | nicotiflorin | (+7.2%) | 6.6% |
| 7 | HYPEROSIDE | quercetin-3-galactoside | 18.4% | 26.2% |
| 8 | SPIRAEOSIDE | quercetin-4'-glucoside | 31.3% | 44.1% |
| 9 | RUTIN | quercetin-3-O-rutinoside quercetin-3-O-glucorhamnoside | 34.7% | 36.0% |
| 10 | KAEMPFERIT-RIN | kaempferol-3,7-di-O-α-L-rhamnoside; 3,4',5,7-tetrahydroxy flavone-3,7-dirhamnoside | 19.8% | 18.4% |
| 11 | QUERCETIN 3-glucoside 5.00 | 3-glucosylquercetin; 3,3',4',5,7-pentahydroxy flavone-3-glucoside | 21.6% | 38.6% |
| 12 | KAEMPFEROL-3-GLUCOSID | 3-glucosylkaempferol; 3,4',5,7-tetrahydroxy flavone-3-glucoside | 18.5% | 11.7% |

Nd: not determined.

Example 2: Inhibitory Effect of a Combination of Phlorizin and LPH Inhibitor on LPH/SGLT1

The effect of a combination of phlorizin and a LPH inhibitor on the uptake of glucose by the SGLT 1 transporter was tested with an ex vivo model that simulates the situation in the human intestine. The ex vivo test model uses tissue from the human small intestine which expresses the lactase phlorizin hydrolase (LPH) and is thus able to cleave phlorizin and other glycosides. Subsequently, the reaction batches that had been pre-processed in this way were tested in an in vitro assay for their inhibitory effect on the SGLT1 transporter.

Human small intestine tissue expressing the lactase phlorizin hydrolase (LPH) was prepared and used as described in Amiri & Naim (J Inherit Metab Dis (2012) 35: 949-954). In summary, so-called "brush border membranes" were prepared from the small intestine and incubated in an appropriate buffer with phlorizin and/or the respective LPH inhibitor for 90 minutes.

Subsequently, the small intestine membranes were separated, and the activity of SGLT1 was determined in the supernatants with a electrophysiological method that was described by Kottra & Daniel (J Pharmacol Exp Ther. 2007; 322 (2): 829-35). Here, Xenopus oocytes were used which express the human SGLT1. The transport of glucose by SGLT1 can be measured because the combined transport of glucose and sodium by SGLT1 causes a current through the oocyte membrane. This current is determined electrophysiologically by a "two-electrode voltage-clamp" method. In this model, a reduction in the activity of the SGLT1 also results in a reduction of current across the cell membrane.
Results:

It was shown that phlorizin and the tested LPH inhibitors reduce the activity of SGLT in a synergistic manner. Table 2 shows the inhibition by the tested compounds with the respective values for the inhibition in percent of original activity. Surprisingly, the combination of phlorizin and the tested LPH inhibitor kaempferol-7-O-glucoside or quercetin-7-glucoside, respectively, was able to reduce the activity of SGLT significantly stronger than the individual substances in sum (see, for example, Batch A). While phlorizin, quercetin-7-glucoside and kaempferol-7-O-glucoside alone in each case reduced the glucose uptake by 32%, 2% or 2.5%, the combinations of phlorizin and quercetin-7-glucoside and phlorizin and kaempferol-7-O-glucoside, respectively, were capable of reducing glucose uptake by 48% and 52%, respectively.

The same effect was also observed when instead of pure phlorizin an apple extract (Batch B) was used which contains 15% phlorizin. This extract inhibited the activity of SGLT by 33%. Quercetin-7-glucoside and kaempferol-7-glucoside alone reduced the activity of SGLT1 by 2.5% and 2.0% in this approach, respectively. In contrast, the combination of apple extract with quercetin-7-glucoside or kaempferol-7-glucoside achieved an inhibition by 49% and 54%, respectively.

TABLE 2

Inhibition of SGLT1-mediated glucose uptake in an ex vivo model

| | Glucose uptake, inhibition |
|---|---|
| Batch A | |
| phlorizin 0.3 µg/ml | 32% |
| quercetin-7-glucoside 10 µg/ml | 2% |
| quercetin-7-glucoside 10 µg/ml & phlorizin 0.3 µg/ml | 48% |
| kaempferol-7-O-glucoside 10 µg/ml | 2.5% |
| kaempferol-7-O-glucoside 10 µg/ml & phlorizin 0.3 µg/ml | 52% |

TABLE 2-continued

Inhibition of SGLT1-mediated glucose uptake in an ex vivo model

| | Glucose uptake, inhibition |
|---|---|
| Batch B | |
| apple extract (with 15% phlorizin) 2 mg/ml | 33% |
| quercetin-7-glucoside 10 µg/ml | 2.5% |
| apple extract (with 15% phlorizin) 2 mg/ml & quercetin-7-glucoside 10 µg/ml | 49% |
| kaempferol-7-O-glucoside 10 µg/ml | 2.0% |
| apple extract (with 15% phlorizin) 2 mg/ml & kaempferol-7-O-glucoside 10 µg/ml | 54% |

The invention claimed is:

1. Composition comprising:
   (a) phlorizin; and
   (b) 0.01 to 10 g of one or more inhibitors of lactase phlorizin hydrolase, wherein the inhibitor is selected from the group consisting of quercetin-7-O-glucoside and kaempferol-7-O-glucoside.

2. Composition according to claim 1, wherein the composition comprises 0.01 to 10 g phlorizin.

3. A method of treating and/or preventing a hyperglycemic disease, comprising administering a composition according to claim 1 to a patient, wherein the disease is selected from the group consisting of adiposity, and diabetes or a disease resulting from diabetes.

4. Pharmaceutical composition, dietary food product or dietary supplement comprising the composition according to claim 1.

5. The method of claim 3, wherein said diabetes is diabetes type II.

6. The method of claim 3, wherein the composition is administered orally, parenterally or topically.

7. The method of claim 3, comprising administering a pharmaceutical composition, dietary food product or dietary supplement comprising the composition according to claim 1 to the patient.

* * * * *